United States Patent [19]
Fritz et al.

[11] Patent Number: 5,342,584
[45] Date of Patent: * Aug. 30, 1994

[54] AIR FRESHENER DEVICE AND CARTRIDGE WITH BATTERY

[75] Inventors: Barbara L. Fritz, Burnsville; John T. Olson, Chisago City; Stephen A. Morganson, Eagan, all of Minn.; William E. Sullivan, Blythewood, S.C.

[73] Assignee: Ecolab Inc., St. Paul, Minn.

[*] Notice: The portion of the term of this patent subsequent to Aug. 10, 2010 has been disclaimed.

[21] Appl. No.: 22,800

[22] Filed: Feb. 23, 1993

Related U.S. Application Data

[63] Continuation of Ser. No. 703,147, May 17, 1991, abandoned, which is a continuation-in-part of Ser. No. 406,724, Sep. 13, 1989, abandoned.

[51] Int. Cl.⁵ ............................................. A61L 9/12
[52] U.S. Cl. ..................................... 422/124; 422/5; 239/51.5; 239/56; 239/58; 206/807; 220/306
[58] Field of Search ................... 422/1, 4, 5, 120-124, 422/300, 306; 239/53-60; 224/902; 294/903; 429/164; 206/333, 807; 220/339, 306, DIG. 20; 215/201

[56] References Cited

U.S. PATENT DOCUMENTS

| | | | |
|---|---|---|---|
| 1,080,716 | 12/1913 | Rand, Jr. | 239/55 |
| 1,496,326 | 6/1924 | Schulte | 239/57 |
| 1,972,368 | 9/1934 | Alex | 55/387 |
| 2,297,984 | 10/1942 | Reller | 220/522 X |
| 2,585,339 | 2/1952 | Miller | 422/124 |
| 2,603,468 | 7/1952 | Sutton | 261/104 |
| 2,614,820 | 10/1952 | Boydjieff | 261/26 |
| 2,615,563 | 10/1952 | Sundberg et al. | 220/522 X |
| 2,629,149 | 2/1953 | Yaffe | 422/124 |
| 3,415,361 | 12/1968 | Adams, Jr. et al. | 220/521 X |
| 3,494,458 | 2/1970 | Meierhoefer | 206/807 X |
| 3,575,346 | 4/1971 | Roth et al. | 239/57 |
| 3,711,023 | 1/1973 | Smith | 239/54 |
| 3,807,082 | 4/1974 | Hautmann et al. | 43/125 |
| 3,908,905 | 9/1975 | Von Philipp et al. | 239/55 |
| 3,990,848 | 11/1976 | Corris | 422/124 X |
| 3,993,444 | 11/1976 | Brown | 422/126 |
| 4,017,030 | 4/1977 | Coplan et al. | 239/145 |
| 4,035,451 | 7/1977 | Tringali | 261/101 |
| 4,059,422 | 11/1977 | Steiner | 422/124 X |
| 4,094,119 | 6/1978 | Sullivan | 53/400 |
| 4,111,654 | 9/1978 | Quincey | 422/124 |
| 4,229,415 | 10/1980 | Bryson | 422/109 |
| 4,271,092 | 6/1981 | Sullivan et al. | 261/30 |
| 4,276,236 | 6/1981 | Sullivan et al. | 261/30 |
| 4,301,095 | 11/1981 | Mettler et al. | 261/30 |
| 4,352,457 | 10/1982 | Weick | 239/45 |
| 4,415,092 | 11/1983 | Boyer | 211/69.1 |
| 4,432,938 | 2/1984 | Meetze, Jr. | 422/49 |
| 4,477,414 | 10/1984 | Muramoto et al. | 422/125 |
| 4,523,870 | 6/1985 | Spector | 454/157 |
| 4,529,125 | 7/1985 | Sullivan | 239/56 |
| 4,576,330 | 3/1986 | Schepp | 220/339 X |
| 4,695,434 | 9/1987 | Spector | 422/116 |
| 4,715,492 | 12/1987 | Holmes | 220/339 X |
| 4,761,008 | 2/1988 | Huggins | 220/555 X |
| 4,840,770 | 6/1989 | Walz et al. | 422/124 X |
| 4,857,240 | 8/1989 | Kearnes et al. | 422/124 X |
| 4,911,296 | 3/1990 | Hart, Jr. | 220/523 X |
| 5,023,020 | 6/1991 | Machida et al. | 422/124 X |
| 5,234,162 | 8/1993 | Sullivan | 422/122 X |

FOREIGN PATENT DOCUMENTS

| | | |
|---|---|---|
| 0485134 | 5/1992 | European Pat. Off. |
| 2556221 | 6/1985 | France |
| 2247823 | 3/1992 | United Kingdom |

*Primary Examiner*—Robert J. Warden
*Assistant Examiner*—E. Leigh Dawson
*Attorney, Agent, or Firm*—Merchant, Gould, Smith, Edell, Welter & Schmidt

[57] ABSTRACT

An air freshener device (200) has a cartridge (100). The cartridge (100) has a housing (101) having a tray (102). A first fragrance (105) is in a first cavity (103) and a second fragrance (106) is in a second cavity (104). A fragrance diffuser (130) is operatively connected to the tray (102) and positioned over the compartments of the tray. A removable cover is operatively connected to the tray to seal the open tops of the cavities. A battery cover (116) has a first side operatively connected to the housing and a second side connected to the housing after a battery is enclosed in the cover.

26 Claims, 12 Drawing Sheets

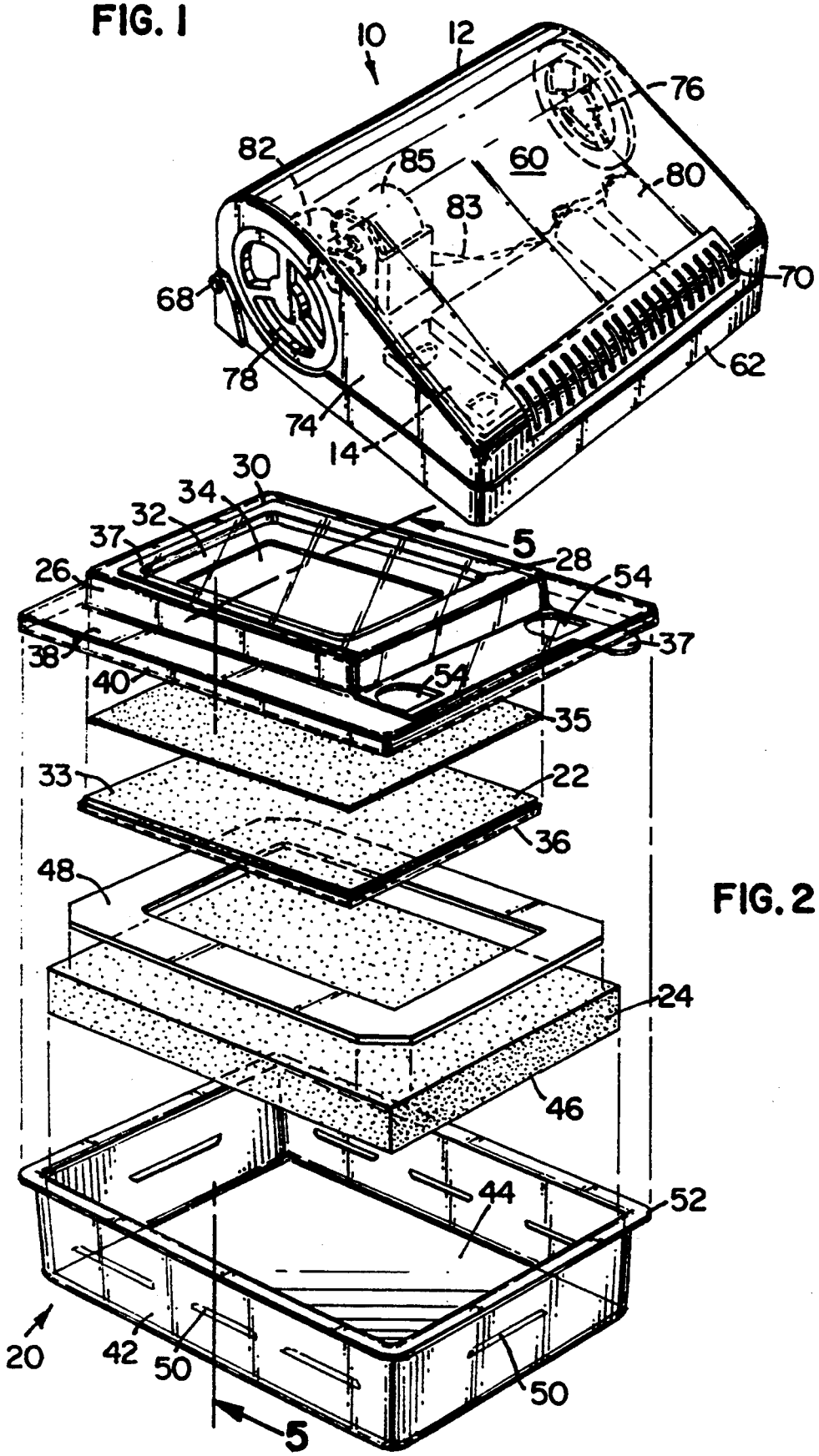

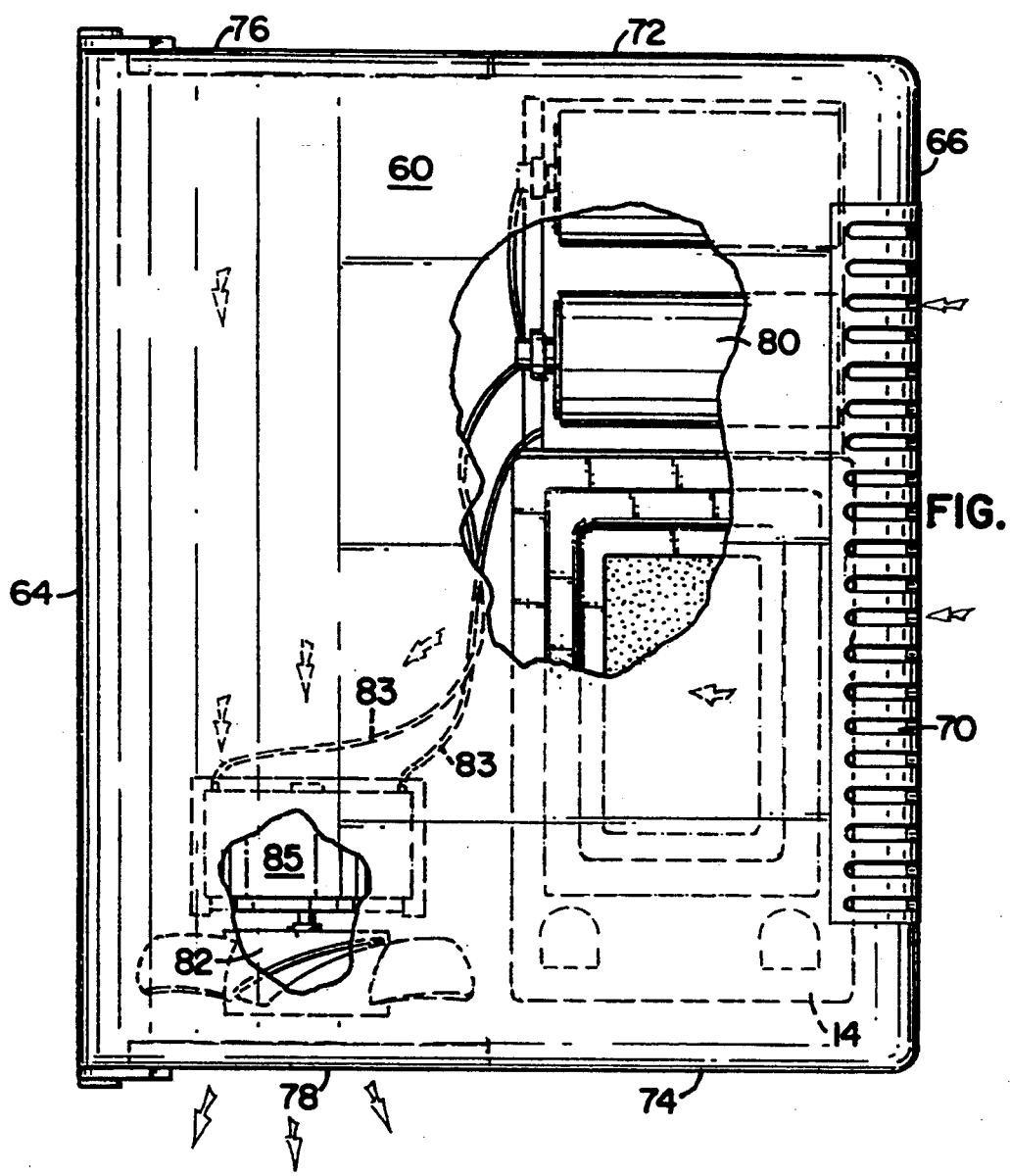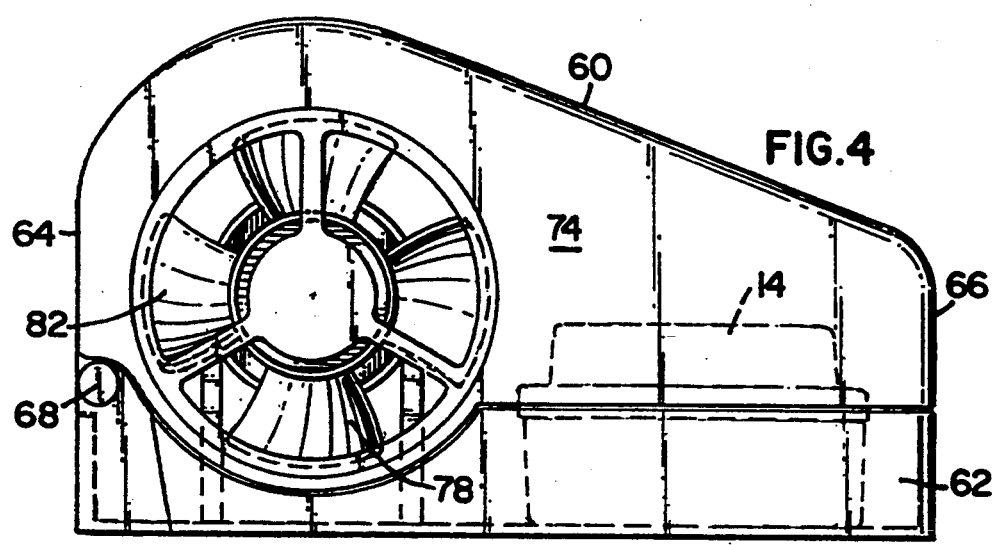

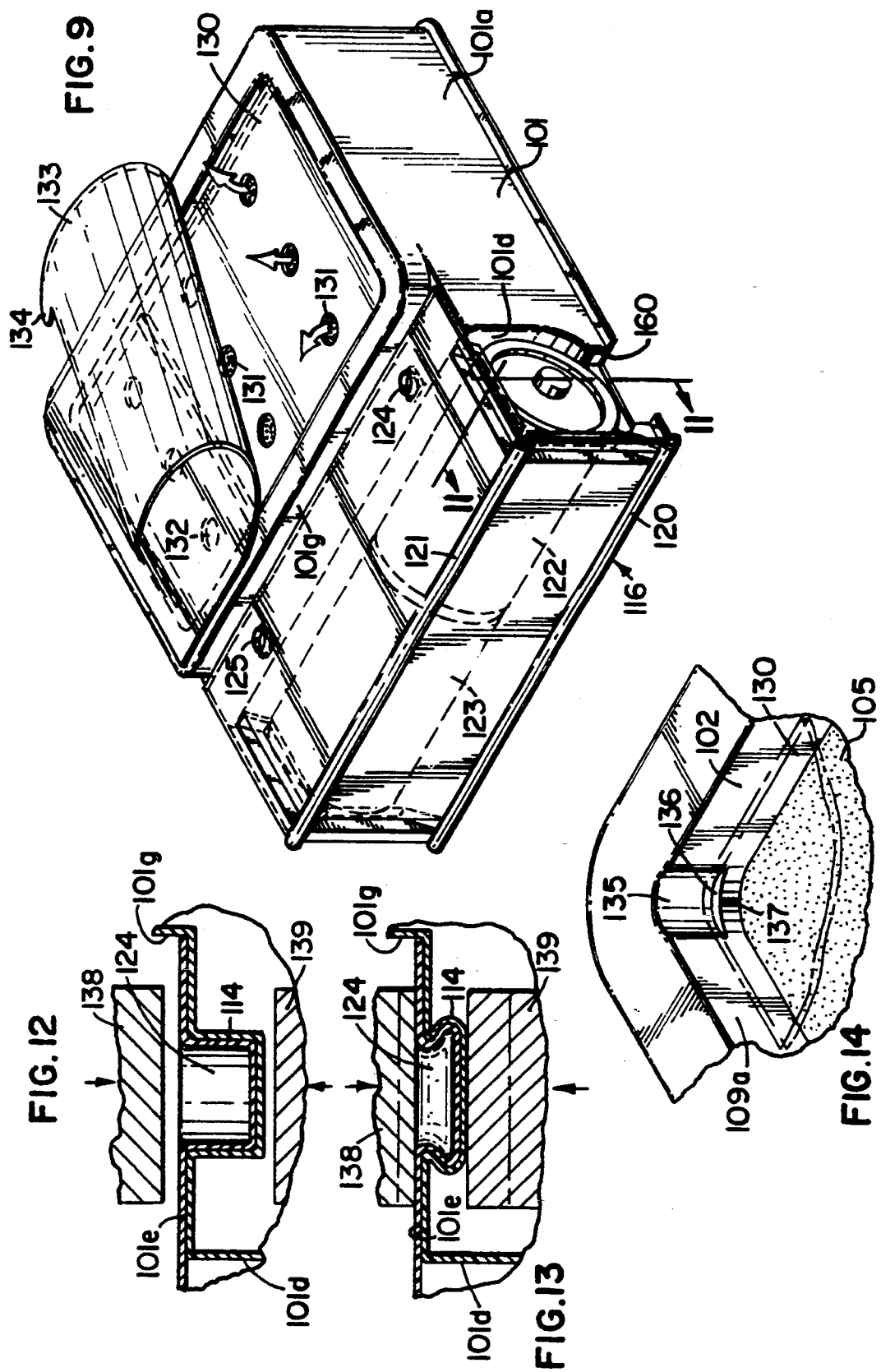

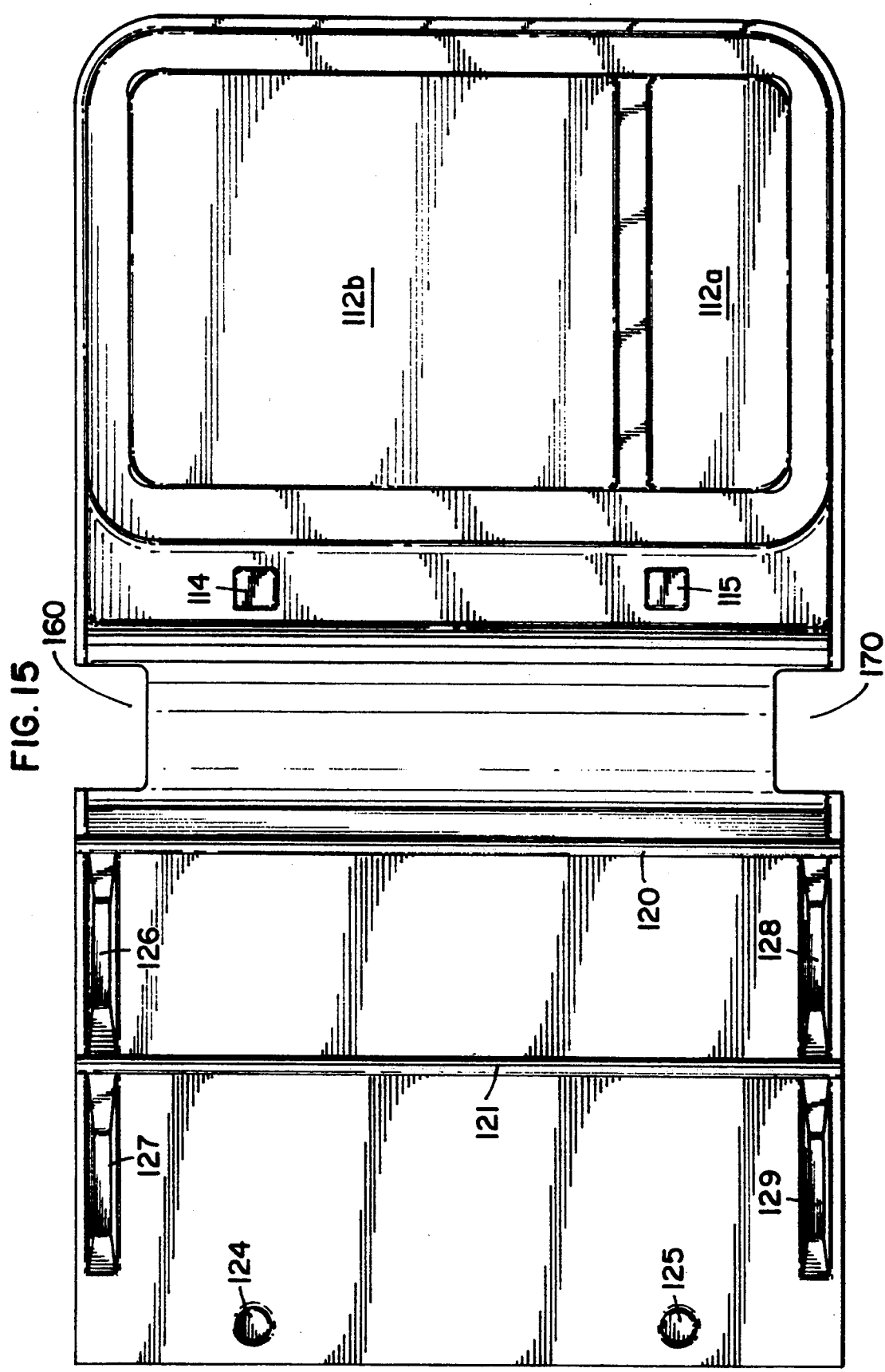

AIR FRESHENER DEVICE AND CARTRIDGE WITH BATTERY

This application is a continuation of U.S. patent application Ser. No. 07/406,724, filed Sep. 13, 1989, abandoned.

BACKGROUND OF THE INVENTION

1. Field of the Invention

This invention relates generally to air freshener devices and cartridges. More particularly, this invention relates to air freshener devices having an evaporation controlled fragrance cartridge which has means for controlling the evaporation of at least two fragrances of different volatilities and the batteries are an integral part of the cartridge.

2. Description of the Prior Art

Air freshener devices which utilize a fan typically direct air flow at the fragrance container. This construction causes the velocity of the air to decrease as it collides with the fragrance container. Therefore, the air flow is weak and thus, the fragrance output of the air freshener apparatus is deficient.

For example, U.S. Pat. No. 4,432,938, issued Feb. 21, 1984 to Murray O. Meetze, Jr., discloses an apparatus for creating a flow of air past a product capable of being vaporized. This apparatus is specifically designed for use with a device that holds the product for release through a permeable membrane. The apparatus includes components for creating a flow of air past or against the device to distribute the volatile product into the environment.

U.S. Pat. No. 4,301,095, issued Nov. 17, 1981 to Leo L. Mettler et al, discloses an air freshener dispenser. The air freshener dispenser disclosed shows an air flow pattern where air enters the housing in all directions and impinges upon a disk which contains the volatile fragrance. The volatilization takes place as the air impinges upon the bottom surface of the pad. The volatilized liquid escapes in a path that is 360° or a total circle at the point of air entry.

These devices direct air flow at the fragrance container. Therefore, the velocity of the air is decreased as it collides with the fragrance container and fragrance flow is impeded.

The present invention utilizes a device where the air flow is not obstructed. Fragrance vapor is drawn into the air stream by the low pressure created by the action of the fan blade. Therefore, the air-fragrance mixture which exits the device enters the environment at a greater velocity thereby aiding in the dispersion of the mixture.

Some types of air fresheners are designed to disperse a combined fragrance which includes fragrances of high and low volatility. The result of the typical design is that the evaporation of the fragrance of high volatility is much greater the first few days of exposure and thereafter evaporation rapidly falls off. This results in a short lived period when the combined fragrances are disseminated at an optimum level. Therefore, it is desirable to control evaporation of the fragrance.

One example where the evaporation of the fragrance is controlled to allow reproduction of a desired odor is U.S. Pat. No. 3,711,023, issued Jan. 16, 1973 to Dean E. Smith. An air conditioning system is disclosed which releases the evaporated volatile substances into the air to produce an odor. The individual compartments from which the odor is to be formed are stored in individual receptacles and the amount of individual components to be released are controllable. The mixing of various components may be controlled by varying the width of the passage way to vary the proportions of the fragrances being mixed. However, the system is not designed to obtain the even rate of evaporation of fragrances of different volatilities.

U.S. Pat. No. 4,477,414, issued Oct. 16, 1984 to Takayoshi Muramoto et al, discloses an apparatus for evaporating a solution of varying volatility (the solution contains ingredients of high, middle, and a low notes). A certain amount of the volatile liquid is allowed to be evaporated at one time. An evaporative container is used which comprises a container for holding the solution and a water absorbing impregnation element that is fitted to the head of the container and which uses the mechanism of a siphon to supply liquid to be evaporated. The use of a controlled dispenser allows the remaining solution to retain the original mixture of notes. This patent also includes a device wherein the amount of evaporation of the solution absorbed to be released can be controlled by a rotating lid. However, this device does not utilize the volatilities of the fragrances by effectively controlling evaporation through separate cavities.

U.S. Pat. No. 3,990,848, issued Nov. 9, 1976, discloses a system for inducing air flow past a gel-type product. A cartridge includes a porous container for holding the product where the cartridge is formed to be received in an air flow induction device that includes a housing having an air admitting opening and an air discharge opening. A fan is mounted in the housing to induct air flow through the opening past the product and out the discharge opening into the environment. A fan is driven by a motor connected to make contact with the terminals of a battery when the cartridge is received in the air flow inducing device. The battery is mounted with and attached to the container of the cartridge. The battery is, however, mounted on top of the container and is exposed to view and is also subject to unauthorized removal. Further, the product being dispensed is a single fragrance.

The present invention addresses the problems associated with the prior art devices and provides an air freshener device that controls evaporation of two fragrances and provides for a cartridge which has the batteries as an integral portion hereof.

SUMMARY OF THE INVENTION

The present invention is a cartridge for use in an air dispenser as well as the combination of a cartridge and dispenser. The dispenser includes a housing defining a cartridge cavity for holding a cartridge. The housing defines a plurality of air passage openings in the housing. A fan is operatively connected to the housing and a motor is operatively connected to the housing and also operatively connected to and adapted to power the fan. A cartridge is positioned in the cartridge cavity.

The cartridge includes a housing and a tray having a first compartment and a second compartment. The first and second compartments have open tops and the tray is operatively connected to the cartridge housing. A first fragrance product, having a first volatility, is positioned in the first compartment and a second fragrance, having a second volatility, is positioned in the second compartment. A fragrance diffuser is operatively connected to the tray and positioned over the compartments. The diffuser has a first set of openings positioned over the first compartment and a second set of openings positioned over the second compartment. A removable cover is operatively connected to the tray to seal the open tops. A battery cover has a first side operatively connected to the housing and a second side having means for connecting the second side to the housing after a battery is enclosed.

In a preferred embodiment, the battery cover is an integral portion of the cartridge and further comprises a locking means to prevent removal of the battery after the cover is closed.

BRIEF DESCRIPTION OF THE DRAWINGS

FIG. 1 is a perspective view of the air freshener device with dashed lines showing the inner workings of the present invention including the fragrance cartridge.

FIG. 2 is an exploded perspective view of the fragrance cartridge of the present invention.

FIG. 3 is a top view of the device of FIG. 1 with break aways to show the fragrance cartridge, power means, and fan.

FIG. 4 is an end view of the device of FIG. 1.

FIG. 9 is a perspective view of the cartridge of FIG. 8, showing the battery cover closed.

FIG. 12 is an enlarged cross-section view of the locking means of the cartridge shown in FIG. 8 before securing the locking means.

FIG. 13 is a cross-section view of the locking means, as shown in FIG. 12, after securing the locking means.

FIG. 14 is an enlarged perspective view of the corner of the tray of the cartridge shown in FIG. 8.

FIG. 15 is a bottom plan view of the cartridge as shown in FIG. 8.

DESCRIPTION OF THE PREFERRED EMBODIMENT

Figure 5:
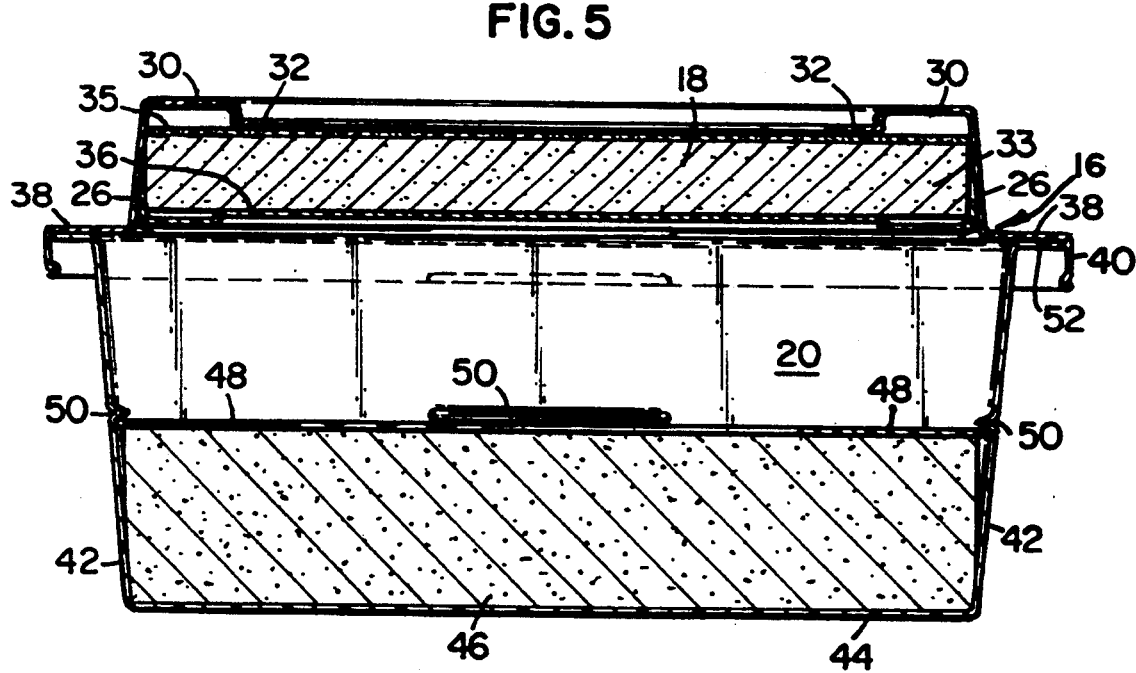
FIG. 5 is a cross sectional view of the fragrance cartridge of FIG. 2 taken along the line 5—5.

Referring to the drawings, wherein like numbers represent like parts throughout the several views, there is generally disclosed at 10 an air freshener device. The apparatus includes a housing 12 and a cartridge 14. The cartridge 14 includes a cartridge housing 16.

Referring to FIGS. 2 and 5, the cartridge housing 16 includes separately sealed first and second cavities 18 and 20. First cavity 18 contains first fragrance 22 having a first volatility. Second cavity 20 contains a second fragrance 24 having a second volatility. The first volatility is lower than the second volatility. The first cavity 18 contains a slow evaporating fragrance or base notes while the second cavity 20 contains a fast evaporating fragrance or top notes. Separately sealing the cavities 18 and 20 prevents mixing of the first fragrance 22 and the second fragrance 24 while in their respective cavities 18 and 20. The cartridge housing 16 is made of a barrier plastic in the preferred embodiment known as Barrex. The barrier plastic does not allow permeation of the fragrances from the cartridge 16 until the user desires to use the cartridge 16.

The first cavity 18 is formed by a continuous outer wall 26, continuous inner wall 28, top wall 30, and wall 32. Continuous outer wall 26 provides the outside boundary for the first cavity 18. Continuous outer wall 26 and continuous inner wall 28 are generally parallel to each other and both are generally perpendicular to top wall 30 and wall 32. Top wall 30 and wall 32 are connected by inner wall 28. These walls 26, 28, 30, and 32 are formed as a single integral unit or first cavity 18. First fragrance 22 is contained in a pad 33 in the preferred embodiment. A diffuser 35 is placed on top of pad 33 to maintain the position, surface, and placement of pad 33, as well as, to act as a diffuser. Pad 33 is made of a non-woven polyester in the preferred embodiment, although it should be understood that any other suitable material may be utilized. The fragrance from pad 33 wicks into diffuser 35 and evaporates from it. The diffuser 35 is made of spun bonded polyester in the preferred embodiment.

Wall 32 is shown with a selectable opening 34 in FIG. 2. The opening 34 is generally rectangular in the preferred embodiment and approximately measures 2⅛ inches by 2⅜ inches. The opening 34 is necessary to allow the first fragrance 22 to escape the cartridge 12. The end user will remove a cover 37 which is sized and configured to fit within or cover the opening 34 and connected to first cavity 18 by an adhesive to allow the first fragrance 22 to escape the sealed first cavity 18. First cavity 18 is separately sealed from second cavity 20 by membrane 36. A lid 38 generally perpendicular to and connected to outer wall 26 in conjunction with membrane 36 seals the first cavity 18 from second cavity 20. A continuous is first lip 40 which generally perpendicular to and connected to lid 38 aids in separately sealing the cavities 18 and 20 which will be discussed in further detail later in this description. Membrane 36, lid 38 and first lip 40 form a single integral unit with first cavity 18. Membrane 36 is a barrier film and is made of a PET film in the preferred embodiment.

Second cavity 20 is formed by a continuous first wall 42 connected to a bottom wall 44. The first wall 42 forms the outside boundary for second cavity 20. The bottom wall 44 is generally perpendicular to the first wall 42 and the connection of these walls 42 and 44 forms the cavity 20. First wall 42 and bottom wall 44 are formed as a single unit or second cavity 20.

The second fragrance 24 is placed in pad 46 in the preferred embodiment and is located in the second cavity 20. The pad 46 is a non-woven polyester in the preferred embodiment. Retainer 48 is placed on the fragrance 24 and pad 46 to hold them in place. The retainer 48 generally forms a ring proximate the continuous first wall 42. The retainer 48 fits under and is kept in place by protrusions 50 in the first wall 42. The retainer 48 is constructed of PET film in the preferred embodiment.

A continuous second lip 52 is formed integrally with the first continuous wall 42 to aid in separately sealing the cavities 18 and 20. First lip 40 is generally formed to mate with second lip 52 to form the cartridge housing 16 which comprises first cavity 18 and second cavity 20. First lip 40 of the first cavity 18 is placed over second lip 52 to form a seal between the cavities 18 and 20. Selectable second openings 54 in the lid 38 provide a means for the second fragrance 24 to escape into the environment. The openings 54 are generally circular in the preferred embodiment and have a diameter of approximately ⅜ inch. The end user will remove cover 37 from the openings 54 to allow the second fragrance 24 to escape the sealed second cavity 20.

As previously discussed, the wall 32 has a selectable opening 34 aligned with cavity 18 while lid 38 has selectable second openings 54 aligned with second cavity 20 thereby providing a means for the fragrances 22 and 24 to exit their respective cavities 18 and 20. The openings 34 and 54 are covered by a removable cover 37. Cover 37 is utilized to retain the fragrances 22 and 24 until the end user removes the cover 37 for use. The removable cover 37 is sized and configured to cover the openings 34 and 54.

In the preferred embodiment, the removable cover 37 must be removed by the end user in order for the fragrances 22 and 24 to escape their respective cavities 18 and 20. The removable cover 37 is peeled off of the cartridge housing 16 where it is attached by an adhesive, thereby exposing the openings 34 and 54. Therefore, when the cover 37 is removed, the fragrances 22 and 24 are free to independently exit their respective cavities 18 and 20. In the preferred embodiment, the cover 37 is a barrier plastic which is heat sealed to the cartridge 14. It should be understood that any other size, configuration or material of cover 37, including separate covers for each opening, may be utilized.

The use of a larger volume of fast evaporating top notes in the second cavity 20 and a smaller volume of slow evaporating base notes in the first cavity 18 allows equalization of the time periods for which the evaporation is optimal. In the preferred embodiment, the slow evaporating base notes have a larger opening 34 allowing for greater evaporation while the top notes have smaller openings 54 allowing slower evaporation. This control of evaporation allows for an air freshener with superior performance.

Figure 6:
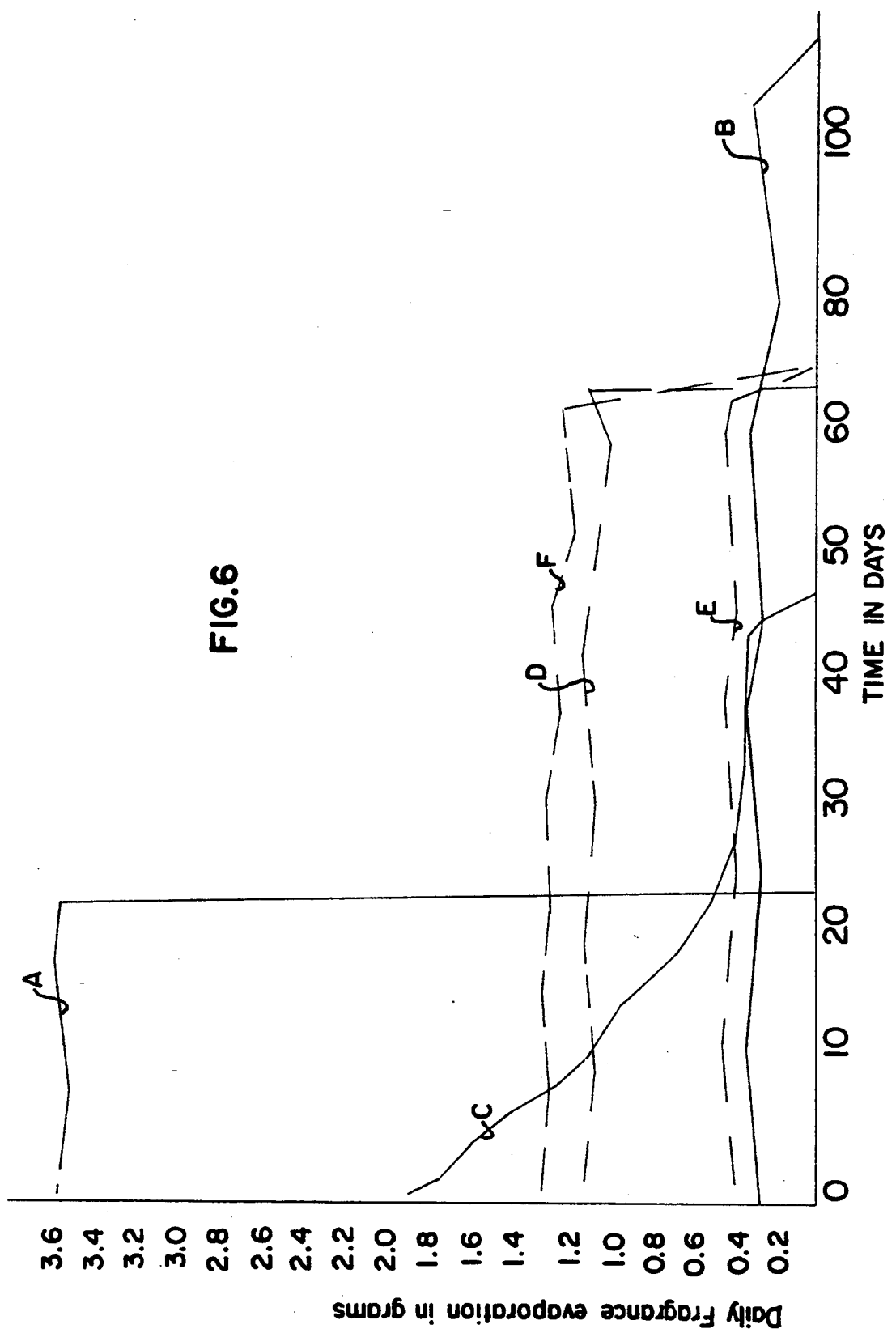
FIG. 6 is a graph of evaporation of fragrance versus time.

As an example, FIG. 6 shows the daily fragrance evaporation in grams versus time in days. Evaporation of the fragrances was measured daily. Fifty percent top notes and fifty percent base notes of cherry fragrance were used to achieve the results in FIG. 6. Cherry fragrance has a vast difference in volatility in top notes and base notes. As shown by line A, the top notes evaporated at a rapid rate, with approximately 3.5 to 3.6 grams evaporating per day. The cherry base notes evaporated quite slowly with an average of approximately 0.2 to 0.4 grams per day over 100 days, as shown by line B, whereas, the top notes evaporated in just over 20 days. Line C demonstrates the poor performance of 50% cherry top notes and 50% cherry base notes as used for a fragrance mixture. Rapid fall off of fragrance output demonstrates the need for evaporation control of the fragrances of high and low volatility.

FIG. 6 also demonstrates an example of the output of the present invention. A large evaporation surface is used for a small volume of expensive base notes while a small evaporation surface is used for a large volume of inexpensive top notes. The fragrances utilized were cherry top notes and cherry base notes. The large volume of cherry top notes escape through the small openings 54. This creates a change in evaporation of the top notes shown by the dashed line D. A small volume of expensive base notes reduces waste when utilized with a large evaporation surface. The daily fragrance evaporation of the base notes is shown by the dashed line E. The present invention reaches a generally level fragrance output by the controlled use of the top and base notes as shown by the dashed line F.

Figure 7:
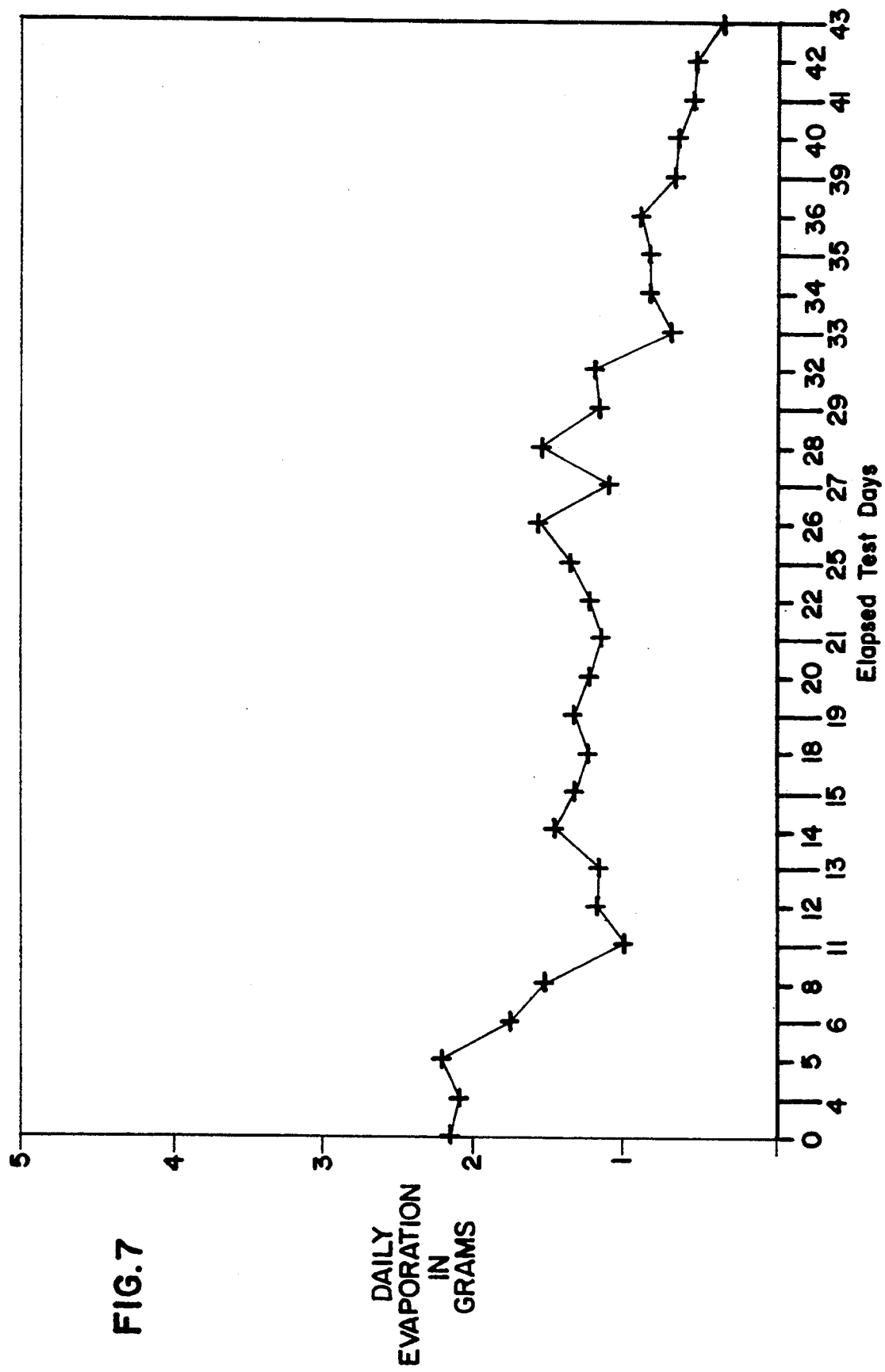
FIG. 7 is a graph of evaporation of fragrance versus time for the present invention.
Figure 8:
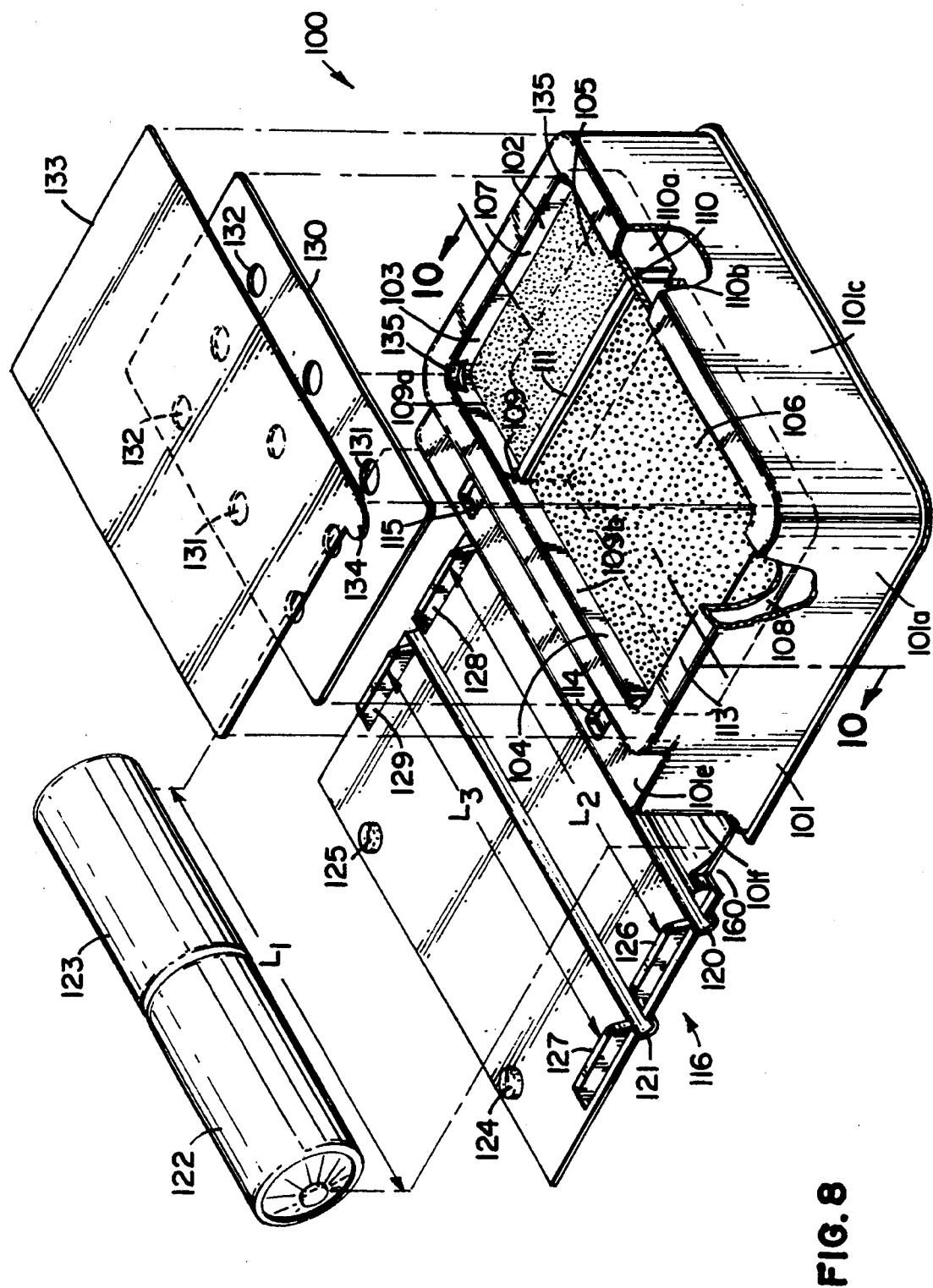
FIG. 8 is a perspective view of a second embodiment of a fragrance cartridge, showing the battery cover is an open position.
Figure 10:
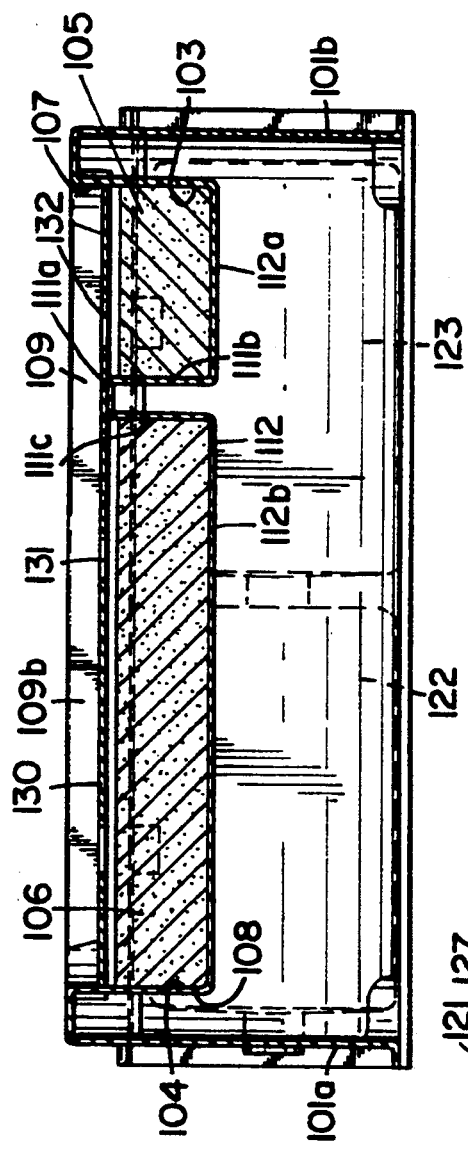
FIG. 10 is a cross-section view of the cartridge shown in FIG. 8, taken generally along the lines 10—10.
Figure 11:
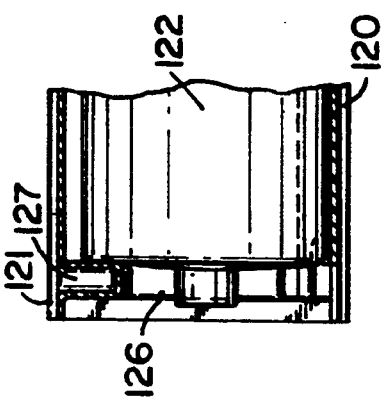
FIG. 11 is an enlarged cross-section view of the cartridge shown in FIG. 9, taken generally along the lines 11—11.

Referring now to FIG. 7, results of a daily evaporation test for the present invention are shown. Fifty grams of cherry top notes were placed in the second cavity 20 and fifteen grams of cherry base notes were placed in first cavity 18. The fifty grams of cherry top notes included 50 grams of benzaldehyde and the fifteen grams of cherry base notes included 7.5 grams of pipernol and 7.5 grams of propylene G. The daily evaporation of the fragrances 22 and 24 were measured by weight. The cartridge 14 was placed in the housing 12 and the device was operated in the standard manner discussed later in this description. The results of this test are shown in FIG. 7. The controlled daily evaporation results in an air freshener having a daily evaporation of approximately 1.2–1.5 grams per day for a large majority of the test period. This controlled evaporation provides a device which provides the user with a longer lasting, constant fragrance output.

The configuration and the number of openings 34, 54 of each cavity 18, 20 is governed by the volatilities of the two fragrances 22, 24, the volumes of the two fragrances 22, 24, and the desired results. The openings 34, 54 are tailored to various fragrances. Different results can be reached with different combinations. For example, using a larger volume of base notes and a smaller volume of high notes will result in different rates of evaporation depending on the area exposed by the openings 34, 54. A greater number of openings in the base note cavity will produce a different result than if the high note cavity had a greater number of openings. Further, different fragrances may permit a smaller volume of fast evaporating top notes in the second cavity 20 and a larger volume of slow evaporating base notes in the first cavity 18 to achieve equalization of the time periods for which the evaporation is optimal.

The volatilities of top notes and base notes may be significantly different. For example, the volatility of Benzaldehyde (1100 microns at 25° C.) compared to the volatility of Ethyl Vanillin (0.15 microns at 25° C.) has a volatility ratio of over 7000 to 1. The following table provides further examples of volatilities of top notes and base notes.

|  | Fragrance Ingredient | Vapor Pressure in Microns at 25° C. Centigrade |
|---|---|---|
| Top Notes | Benzaldehyde | 1100 |
|  | Spearmint oil | 250 |
|  | Limonene | 950 |
|  | Pinenedle oil Siberian | 580 |
|  | Methyl Salicylate | 118 |
| Base Notes | Citral | 58 |
|  | Carvone | 95 |
|  | Ethyl Vanillin | 0.15 |
|  | Emp Glicidate | 3 |

Referring to FIGS. 1, 3 and 4, the outer housing 12 includes cover member 60 and a base member 62. The housing 12 is made of polycarbonate material such as Lexan in the preferred embodiment. It should be understood that other materials such as ABS plastic or Cycalac may be used. Cover member 60 has a first side 64 and a second side 66. In the preferred embodiment, a hinge 68 located proximate the first side 64 is used to pivotally secure cover member 60 to base member 62. This pivotal connection allows access to the inner workings of the device 10.

A first air passage opening 70 is located proximate the second side 66 of cover member 60. The first air passage opening 70 consists of a plurality of generally rectangular slots in the preferred embodiment. Cover member 60 also includes a top 72 and a bottom 74. The top 72 and bottom 74 respectively include second and third air passage openings 76 and 78. The air passage openings 76 and 78 are generally circular in cross section and are divided into three separate generally triangular portions in the preferred embodiment. It should be understood that other configurations of air passage openings may be utilized in the present invention.

Base member 62 is adapted and configured to be mounted on a surface. For example, the base member 62 may be mounted above a door so the user is exposed to the fragrance when entering a room. As shown in FIG. 3, base member 62 contains the fragrance cartridge 14. The cartridge 14 is placed such that small openings 56 are proximate the bottom 74 and the cartridge 14 is adjacent second side 66 of the cover member 60 in the preferred embodiment. Power means 80 are also connected to base member 62. In the preferred embodiment, the power means 80 are batteries, but it should be understood that any other suitable means to supply power may be utilized. The power means 80 supply power to a fan 82 by means of wires 83 which connect them. The power means 80 are positioned proximate second side 66 and away from the air flow path between air passage openings 76 and 78. The fan 82 is positioned so as to be proximate the bottom 74 of cover member 60 and aligned with the air passage openings 76 and 78. The fan 82 is connected to the base member 62 in the preferred embodiment. The fan 82 includes a motor 85. In the preferred embodiment, the motor 85 is a 3 volt motor driven by two 1.5 volt batteries resulting in a fan having 600 rpm. However, it should be understood that any other placement of fan 82 or power means 80 which follows in the spirit of the present invention may be utilized.

After the user has removed the cover 37 to open the selected openings 34 and 54 exposing the fragrances 22 and 24 of cavities 18 and 20, the cartridge 14 is ready for use. As previously discussed, the size and number of openings 34 and 54 are predetermined. The removal of the cover 37 to open openings 34 and 54 to expose fragrances 22 and 24 allows control of the rate of evaporation, as well as the mixing of the fragrances 22 and 24.

The power means 80 powers the fan 82. The fan 82 creates an unobstructed air flow between the second and third air passage openings 76 and 78. The air enters the second air passage opening 76 and flows toward the third air passage opening 78 and then exits the third air passage opening 78. This air flow is not obstructed by the fragrance cartridge 14 or the power means 80. Air is also drawn into the device through the first air passage opening 70. This air moves over the fragrance cartridge 14 picking up fragrances 22 and 24. This air-fragrance mixture is drawn into the unobstructed air stream between the second and third air passage openings 76 and 78 by the low pressure created by the action of the fan 82. The air-fragrance flow is shown by arrows in FIG. 3. This side venting of the fragrances to the fan blade and the unobstructed flow allow dual air flow and allow the air-fragrance mixture to exit the device easily and to enter the environment at a greater velocity which aids in the dispersion of the mixture. The negative pressure created at the back of the fan 82 may create a turbulence which causes a portion of the air-fragrance mixture to exit the device 10 through the first air passage opening 70.

When the fragrance cartridge 14 has expired, it may be replaced by a refill cartridge which is identical to the fragrance cartridge 14. The refill cartridge is placed in the same position as the expired cartridge.

It should be understood that although the invention has been described as having a top, bottom and sides for purposes of clarity, any suitable orientation of the apparatus may be used.

Referring to FIGS. 8-15, there is shown a second embodiment of a fragrance cartridge, generally designated as 100. The cartridge 100 includes a cartridge housing 101. The cartridge housing 101 includes a tray 102 which has a first cavity 103 and a second cavity 104. The first cavity 103 contains a first fragrance 105 having a first volatility and the second cavity 104 contains a second fragrance 106 having a second volatility, the first volatility being lower than the second volatility. The first cavity 103 contains a slow evaporating fragrance or base notes while the second cavity 104 contains a fast evaporating fragrance or top notes.

The tray 102 has a top wall 107 and bottom wall 108 operatively connected by sidewalls 109 and 110. The sidewall 109 has a first portion 109a and a second portion 109b. Similarly, the other sidewall 110 has a first portion 110a and a second portion 110b. A divider 111 separates the first cavity 103 from the second cavity 104. The divider 111 has a top wall 111a operatively connected to sidewalls 111b and 111c. A bottom 112 has a first portion 112a and a second portion 112b. It can therefore be seen that the first cavity 103 has an open top and is defined by the bottom 112a, top wall 107, sidewall 111b, side portion 109a and side portion 110a. Similarly the second cavity 104 is defined by the bottom portion 112b, second portion 109b, second portion 110b, bottom wall 108 and sidewall 111c. The tray 102 has a flat rim 113 which extends around all four sides of the tray 102.

The housing 101 has bottom wall 101a, top wall 101b operatively connected by first sidewall 101c and second sidewall 101d. The second sidewall 101d has a flat planar surface 101e connecting to generally upright portions 101f and 101g. The flat planar surface 101e has two generally square depressions 114 and 115 formed therein.

A battery cover is generally designated as 116. The battery cover 116 has three generally rectangular segments 117, 118 and 119. The first segment 117 has a first side operatively connected to portion 101f and a second side operatively connected to the second segment 118. The second segment 118 has its other side operatively connected to the third segment 119. Segment 117 is operatively connected to segment 118 by means of a U-shaped hinge 120 and similarly the second segment 118 is operatively connected to the third segment 119 by means of a second U-shaped hinge 121. The hinges 120 and 121 allow for the segments to be bent 90° with respect to each other and, as will be described more fully hereafter, form a cover for the batteries 122 and 123. The first segment 117 has a generally concave surface for supporting the batteries 122 and 123. Two generally cylindrical locking tabs 124 and 125 are formed on the inside surface of the third segment 119. The locking tabs 124 and 125 are sized and positioned to have a slight friction fit with the depressions 114 and 115, respectively. Referring to FIG. 12, it can be seen how the tab 124 fits inside the depression 114. There is a slight friction fit between the two. Locking bars 126 and 128 are formed at the ends of the second segment 118 and locking bars 127 and 129 are formed at the ends of the third segment 119. The length $L_1$ of the batteries 122 and 123 is equal to the distance $L_2$ and $L_3$ which are the distances between the locking bars 126 and 128 as well as 127 and 129. The function of the locking tabs 124 and 125 as well as the locking bars 126–129 will be more fully described hereafter.

A fragrance diffuser 130 is sized to fit over the open tops of the cavities 103 and 104 and has a slight friction fit with the tray. The diffuser 130 rests across the top wall 111a of divider 111. In the four corners, the diffuser 130 rests on four support sections. Referring to FIG. 14, it can be seen at the intersection of the walls that there is a portion 135 which has a smaller radius than the portion 137. Therefore, a small lip or protrusion 136 is formed. This lip 136 is present in all four corners and further supports the four corners of the diffuser 130. A first set of openings 132 are formed in the diffuser and are located above the first cavity 103. A second set of openings 131 are formed in the diffuser above the second cavity 104. The size of the openings 131 and 132 will be dependent upon the particular volatility of the fragrances 105 and 106 utilized in the cartridge 100. The openings 131 and 132 would be sized to allow the fragrances to evaporate at a rate such that the fragrances would be used up at approximately the same time. A lid 133 is heat sealed to the rim 113 and seals the fragrances 105 and 106 within the tray 102. The lid 133 is preferably a polyester aluminum foil lid with a heat seal coating. The lid has a tab 134 attached thereto so that the lid may be peeled off of the rim 113.

The fragrances 105 and 106 may be any suitable fragrance, such as those disclosed with respect to the first embodiment. As shown in the second embodiment, the fragrances are entrapped in either a wax or gel and preferably the carrier is sodium stearate. One skilled in the art will recognize that placing the fragrances in a different matrix (a wax or gel) other than in the first embodiment (a pad), will require the empirical selection of the proportions of the fragrance, matrix and diluent to result in the required release characteristics.

In assembling the cartridge 10, the fragrances 105 and 106 are placed in their respective cavities 103 and 104. Then, the diffuser 130 is placed over the open top. Then the lid 133 is heat sealed to the rim 113, thereby sealing in the fragrances 105 and 106. Batteries 122 and 123 are placed on the concave surface of the first segment 117. The third segment 119 is then rotated so that the locking tabs 124 and 125 are placed in the depressions 114 and 115. This configuration is shown in FIG. 9. The locking bars 126–129 prevent lateral movement of the batteries 122 and 123. The locking bars 126–129 are sized such that when in the configuration shown in FIG. 9, the batteries 122 and 123 can not be removed out of the open ends. This is shown more clearly in FIG. 11. There, the locking bar 127 is shown to be sized such that the distance from the bottom of the locking bar 127 to the first segment 119 is less than the width of the battery 122. Similarly, the distance from the locking bar 126 to the portion 101f is less than the width of the battery 122. The same configuration is applicable for locking bars 128 and 129. This prevents the batteries being removed from the open ends as shown in FIG. 9. The third segment 119 is presently just being held in place by a friction fit of the locking tabs 124 and 125. To further secure the cover, the tabs 124 and 125 are placed through a crushing operation.

Referring to FIGS. 12 and 13, it can be seen how the tab 124 originally has a friction fit with the depression 114. This is shown in FIG. 12. Then, two presses 138 and 139 are brought into contact with the cartridge 100. The first press is placed across the flat planar surface 101e. The second press 139 is brought up underneath the housing to contact the bottom of the depression 114. The presses 138 and 139 are then brought closer together, deforming the tab 124 as well as the depression 114. This crushing position is shown in FIG. 13. The effect of the crushing of the tab and depression is to expand outward the depression and tab. However, the size of the opening at the top of the depression is not affected while the tab and body of the depression assume a more elongated form. This elongated form is larger than the opening at the top and therefore form a secure lock on the battery cover 116. This lock, in combination with the locking bars 126–129 prevent the easy or unauthorized removal of the batteries 122 and 123. The batteries can then only be removed by destroying the battery cover. These features greatly reduce the chance of theft of the batteries when the cartridge is being inserted. These cartridges are typically used in commercial installations and there is a serious problem of the batteries being removed by either employees or customers.

The housing 101, tray 102 and battery cover 116 are preferably formed as an integral, one-piece unit. The material may be made of any suitable barrier plastic such as Barrex. The barrier plastic, along with the foil lid 133, do not allow permeation of the fragrances from the cartridge 100 until the user desires to use the cartridge 100. Then, it is simply an easy matter of grasping the tab 134 and removing the foil lid. The cartridge 100 may then easily be inserted into the dispenser 150 without the user coming in contact with the fragrances.

Figure 16:
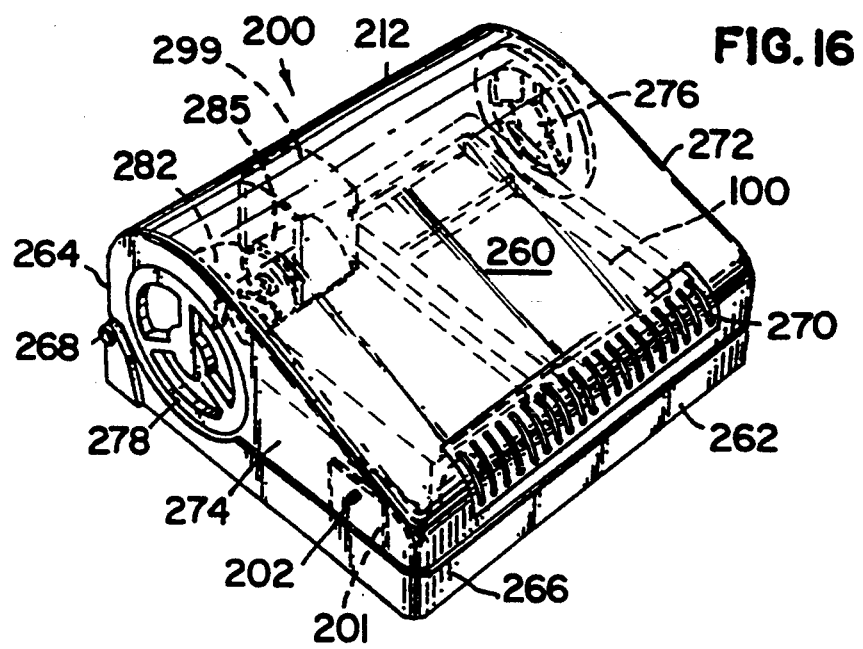
FIG. 16 is a perspective view of a second embodiment of an air freshener device with dashed lines showing the inner workings of the present invention including the second embodiment of the fragrance cartridge.

Referring to FIG. 16, there is generally disclosed another air freshener device 200 which includes a housing 212 and the cartridge 100. The housing 212 has been modified slightly, in comparison to the housing 12, to allow for the different sized cartridge 100. In addition, there has been the addition of a timing circuit 201 and an LED 202, as will be described more fully hereafter. The housing 212 is modified to allow the cartridge 100 to be positioned underneath the fan 285. The fan 285 is now suspended from the cover member 260. Any suitable means of suspending the fan may be utilized, such as by gluing a support structure 299 to the top of the cover and then mounting the fan 85 to the support structure 299. Due to the different configurations of the batteries 122 and 123, it is also necessary to reconfigure the electrical contacts. Otherwise, the housing 212 is quite similar to the housing 12. The housing 212 is made of a polycarbonate material such as Lexan as in the preferred embodiment. The cover member 260 has a first side 264 and a second side 266. A hinge 268 is located proximate the first side 264 and is used to pivotally secure the cover member 260 to the base member 262.

This pivotal connection allows access to the inner workings of the device 200.

A first air passage opening is located proximate the second side 266 of cover 260. A first air passage opening 270 consists of a plurality of generally rectangular slots. Cover member 260 also includes a top 272 and a bottom 274. The top 272 and bottom 274 respectively include second and third air passage openings 276 and 278. The air passage openings 276 and 278 are generally circular in cross section and are divided into three separate generally triangular portions in the preferred embodiment. It should be understood that other configurations of air passage openings may be utilized in the present invention.

Figure 17:
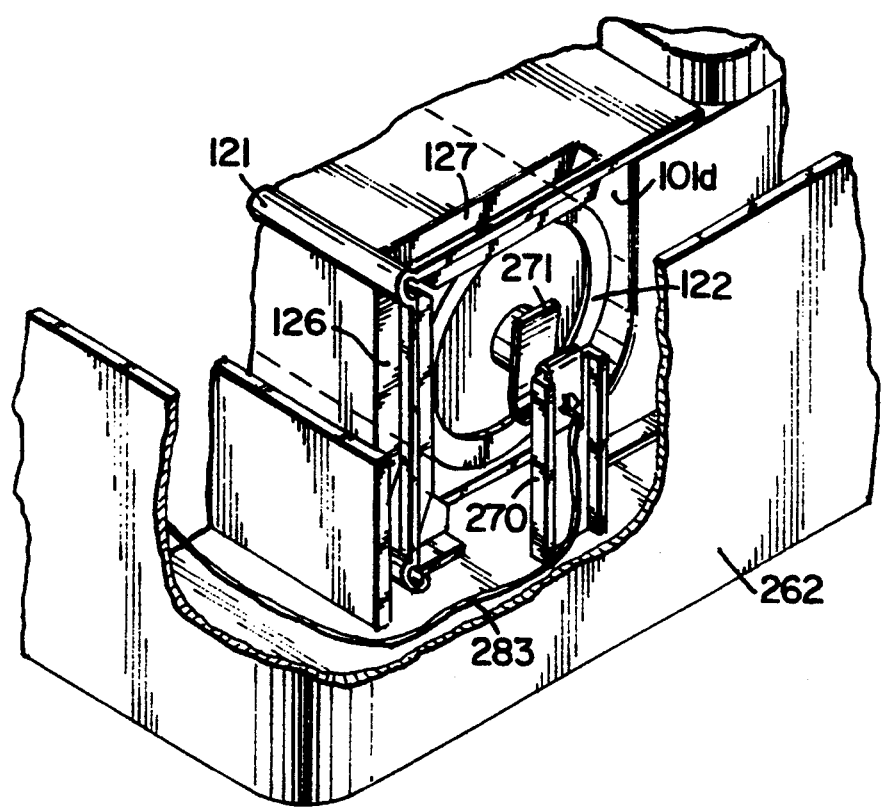
FIG. 17 is an exploded perspective view showing the electrical connections with the battery.

The base member 262 is adapted and configured to be mounted on a surface, similar to base member 62. The batteries 122 and 123 supply power to a fan 282 by means of wires 83 which connect them. The fan 282 is positioned so as to be proximate the bottom 274 of the cover member 260 and aligned with the air passage openings 276 and 278. The fan 282 includes a motor 285. In comparison to the housing 12, it was necessary to reconfigure the electrical connection means with the wires 283. Referring to FIG. 15, it can be seen that there are two cutouts 160 and 170 formed in the housing 101. These cutouts are utilized in order to allow the cartridge 100 to be easily slid into the housing 212 and make electrical contact. In inserting the cartridge 100, the top portion of the cartridge is slid into the dispenser and underneath the motor and fan. The cartridge is then pushed downward and electrical contact is made at the positive end of battery 122 and the negative end of battery 123. The means of making contact are similar and a more detailed view of the positive contact is shown in FIG. 17.

A plastic mounting member 270 is operatively connected to the inside surface of the base 262. A metal clip 271 has a snap fit over the top of the mounting member 270. The clip 271 has suitable connections for connecting the wires 283 which go to both the motor 285 and the timing circuit. Similarly, the negative end has a similar clip so that the wires 283 may be connected to the motor and timing circuit.

Figure 18:
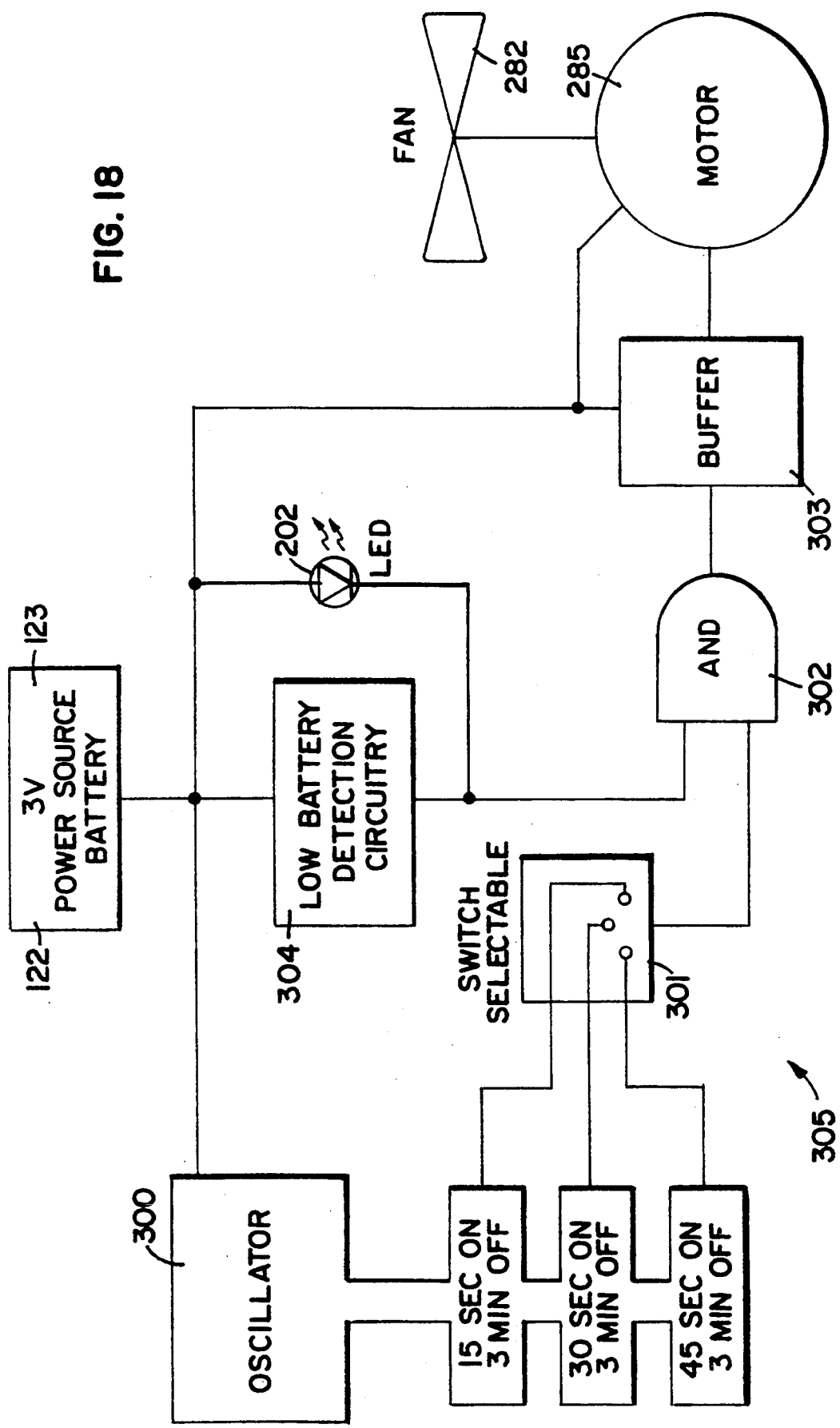
FIG. 18 is a block diagram of the electrical portion of the second embodiment shown in FIG. 16.

Referring next to FIG. 18, a preferred embodiment circuit 305 for driving the fan 282 is illustrated. As noted, two batteries 122, 123 provide a three volt power source. The batteries 122, 123 are connected to an oscillator circuit 300. The oscillator circuit 300 provides for various duty cycles which may be selected via switch 301. Preferably, the oscillator is of the RC/IC type, for example, provided by the chip having the designation 74HC4060. In a preferred embodiment, three duty cycles are provided including: fifteen seconds on-three minutes off, thirty seconds on-three minutes off, and forty five seconds on-three minutes off. It will be appreciated that these duty cycles are illustrative only.

Monitoring the voltage provided by batteries 122, 123 is a low battery detection circuit 304. The detection circuit 304 is preferably provided by an MAX211CPA chip. In essence, the circuit 304 functions as a short circuit when the battery 122, 123 voltage is above a certain threshold value, and functions as an open circuit when the battery voltage drops below the threshold value. In parallel with the detection circuit 304 is LED 202.

Therefore, those skilled in the art will appreciate that in operation when the battery 122, 123 provides a three volt output, detection circuit 304 acts as a short circuit providing three volts at point A. Those skilled in the art will recognize that until the battery 122, 123 voltage drops below the threshold value, the battery 122, 123 voltage and the voltage at point A will be equal. Since there is no voltage drop across the detection circuit 304, the LED 202 does not light and the first input to AND gate 302 from detection circuit 304 is high. The second input to gate 302 is connected to selectable switch 301. Therefore, when the duty cycle provided by oscillator 300 is also high, AND gate 302 provides a high signal to buffer 303. Buffer 303 is thereby turned on and provides a positive voltage to motor 285, driving fan 282. Preferably, the buffer 303 electrically isolates the AND gate 302 and drives the motor 285. Buffer 303 in a preferred embodiment is a transistor having the designation 2N2222A.

Alternatively, those skilled in the art will appreciate that the AND gate 302 output goes low when the duty cycle goes low, turning off the buffer 303 and removing the positive voltage from the motor 285.

When voltage source 122, 123 goes below a predetermined threshold value, low battery detection circuit 304 functions as a voltage drop, thereby lowering the voltage at point A, whereby LED 202 turns on (i.e. it emits light providing an indication of the low voltage condition). When point A is low, AND gate 302 can not provide a high output to buffer 303, and in turn, buffer 303 can not provide a positive voltage to motor 285. Thus, when a low voltage condition occurs, fan 282 will not be driven.

Although not detailed, it should be well understood by those skilled in the art that the various components and devices illustrated in FIG. 18 are to be properly connected to appropriate voltage sources, etc., so as to operate in their intended manner.

Other modifications of the invention will be apparent to those skilled in the art in light of the foregoing description. This description is intended to provide specific examples of individual embodiments which clearly disclose the present invention. Accordingly, the invention is not limited to those embodiments for the use of elements having specific configurations and shapes as presented herein. All alternative modifications and variations of the present invention which follow in spirit and broad scope of the appended claims are included.

We claim:

1. A cartridge for use in a dispenser, said cartridge comprising:
   (a) a housing;
   (b) a tray having a first compartment and a second compartment, said first and second compartments having an open top, said tray operatively connected to said housing;
   (c) a first fragrance product having an outer surface area and having a first volatility positioned in said first compartment, said first compartment exposing less than all of the surface area of said first fragrance product;
   (d) a first fragrance product having an outer surface and having a second volatility positioned in said second compartment, said compartment exposing less than all of the surface area of said second fragrance product;
   (e) a fragrance diffuser operatively connected to said tray and positioned over said compartments, said diffuser having a first set of openings positioned over said first compartment and a second set of openings positioned over said second compartment;

(f) a removable cover operatively connected to said tray to seal said open tops, said removable cover is operably connected to said tray to be operably removed to expose both said first and second sets of openings, thereby allowing said first and second fragrance products to simultaneously exit from said first and second sets of openings respectively;

(g) a battery cover, said battery cover having a first side operatively connected to said housing and a second side having means for connecting said second side to said housing after a battery is enclosed in said cover;

(h) a battery supported by said battery cover, said battery positioned to contact the electrical connection means when said cartridge is inserted in said cavity;

(i) said battery cover comprises: (i) a base member operatively connected to said housing, said base member providing a support base to said battery; (ii) a side member operatively connected to said base member; and (iii) a top member, having first and second sides, said first side operatively connected to said side member and said second side operatively connected to said housing; and (j) lock means to retain said battery after said battery cover is closed.

2. The cartridge of claim 1, wherein said diffuser is operatively connected to said tray and said diffuser having an element sized to have a snap fit with respect to a second element of said tray, said element and said second element mated together to form a snap fit, and said tray having protrusions positioned above a level of said products, said diffuser supported by said protrusions and said snap fit.

3. The cartridge of claim 1, wherein said battery cover 35 is an integral portion of said cartridge.

4. The cartridge of claim 1, wherein said lock means comprises:
(a) a locking bar positioned proximate said cover's front;
(b) a locking bar positioned proximate said cover's back, wherein when said cover is closed, said locking bars prevent longitudinal movement along said battery's longitudinal axis; and
(c) means for securing said second side to said housing.

5. The cartridge of claim 1, wherein said first and second fragrance products comprise a fragrance entrapped in a gel.

6. The cartridge of claim 1, wherein said first and second fragrance products comprise a fragrance entrapped in a wax.

7. The cartridge of claim 1, wherein said first and second fragrance products comprise a fragrance entrapped in sodium stearate.

8. The cartridge of claim 1, wherein said tray has a continuous wall, having a top edge, operatively connected to a bottom wall and a flat sealing lip operatively connected to said top edge.

9. The cartridge of claim 8, wherein said removable cover is a combination of polyester and aluminum foil having a heat seal coating, wherein said removable cover is heat sealed to said flat sealing lip.

10. The cartridge of claim 1, wherein said outer surface of said first fragrance product has a top surface and said first compartment exposing only the top surface area of said first fragrance product and said second fragrance product having a top surface area and said compartment exposing only said top surface area of said second fragrance product.

11. The cartridge of claim 1, wherein said lock means prevents removal of said battery.

12. The cartridge of claim 11, wherein said securing means comprises:
(a) a receiving cavity formed in said housing, said receiving cavity having an opening at its top;
(b) a locking tab operatively connected to said top member, said tab positioned to be inserted in said receiving cavity when said cover is closed;
(c) said tab sized to form a friction fit in said receiving cavity; and
(d) said tab and housing deformable under pressure, wherein when said cover is closed and pressure is applied to both the top and bottom of said tab and housing proximate said receiving cavity, said housing and tab are compressed and deform to a size larger than said opening of said receiving cavity wherein said cover may not be removed without breaking said cover.

13. An air freshener dispenser comprising:
(a) a housing defining a cartridge cavity for holding a cartridge and a plurality of air passage openings in said housing;
(b) a fan operatively connected to said housing;
(c) a motor operatively connected to said housing and operatively connected to and adapted for driving the fan;
(d) a cartridge positioned in said cartridge cavity, said cartridge comprising:
 (i) a housing;
 (ii) a tray having a first compartment and a second compartment, said first and second compartments having an open top, said tray operatively connected to said housing;
 (iii) a first fragrance product having an outer surface area and having a first volatility positioned in said first compartment, said first compartment exposing less than all of the surface area of said first fragrance product;
 (iv) a second fragrance product having an outer surface area and having a second volatility positioned in said second compartment, said second compartment exposing less than all of the surface area of said second fragrance product;
 (v) a fragrance diffuser operatively connected to said tray and positioned over said compartments, said diffuser having a first set of openings positioned over said first compartment and a second set of openings positioned over said second compartment;
 (vi) a removable cover operatively connected to said tray to seal said open tops, said removable cover is operably connected to said tray to be operably removed to expose both said first and second sets of openings, thereby allowing said first and second fragrance products to simultaneously exit from said first and second sets of openings respectively;
 (vii) a battery cover, said battery cover having a first side operatively connected to said housing and a second side having means for connecting said second side to said housing after a battery is enclosed in said cover;

(h) a battery supported by said battery cover, said battery positioned to contact said electrical connection means when said cartridge is inserted in said cavity;

(i) said battery cover comprises:
  (i) a base member operatively connected to said housing, said base member providing a support base to said battery;
  (ii) a side member operatively connected to said base member; and
  (iii) a top member, having first and second sides, said first side operatively connected to said side member and said second side operatively connected to said housing, (j) lock means to retain said battery after said cover is closed; and (k) whereby when the motor powers said fan the air passage openings receive air which moves through the housing and where some of the air received picks up the fragrance from said first and second product resulting in an air-fragrance mixture which is drawn into the air flow and exits the housing allowing dispersion of the fragrance.

14. The dispenser of claim 13, wherein said diffuser is operatively connected to said tray and said diffuser having an element sized to have a snap fit with respect to a second element of said tray, said element and said second element mated together to form a snap fit, and said tray having protrusions positioned above a level of said products, said diffuser supported by said protrusions and said snap fit.

15. The dispenser of claim 13, wherein said battery cover is an integral portion of said cartridge.

16. The dispenser of claim 13, wherein said lock means comprises:
  (a) a locking bar positioned proximate said cover's front;
  (b) a locking bar positioned proximate said cover's back, wherein said cover is closed, said locking bars prevent longitudinal movement along said battery's longitudinal axis; and
  (c) means for securing said second side to said housing.

17. The dispenser of claim 13, wherein said first and second fragrance products comprise a fragrance entrapped in a gel.

18. The dispenser of claim 13, wherein said first and second fragrance products comprise a fragrance entrapped in a wax.

19. The dispenser of claim 13, wherein said first and second fragrance products comprise a fragrance entrapped in sodium stearate.

20. The cartridge of claim 13, wherein said ray has a flat sealing lip.

21. The cartridge of claim 20, wherein said removable cover is a combination of polyester of polyester and aluminum foil having a heat seal coating, wherein said removable cover is heat sealed to said flat sealing lip.

22. The dispenser of claim 13, further comprising a timing circuit said timing circuit operatively connected to said fan, wherein the fan is operated intermittently to reduce the overall power consumption.

23. The dispenser of claim 22, further comprising a light emitting diode operatively connected to a low voltage detector, wherein the light emitting diode will light once the voltage from the battery reaches a preset level so as to indicate that batteries have reached a predetermined value and further comprising means to turn off said motor when said 24. The dispenser of claim 13, wherein said outer surface of said first fragrance product has a top surface and said first compartment exposing only the top surface area of said first fragrance product and said second fragrance product having a top surface area and said compartment exposing only said top surface area of said second fragrance product.

25. The dispenser of claim 13, wherein said lock means prevents removal of said battery.

26. The dispenser of claim 25, wherein said securing means comprises:
  (a) a receiving cavity formed in said housing, said receiving cavity having an opening at its top;
  (b) a locking tab operatively connected to said top member, said tab positioned to be inserted in said receiving cavity when said cover is closed;
  (c) said tab sized to form a friction fit in said receiving cavity; and
  (d) said tab and housing deformable under pressure, wherein when said cover is closed and pressure is applied to both the to and bottom of said tab and housing proximate said receiving cavity, said housing and tab are compressed and deform to a size larger than said opening of said receiving cavity wherein said cover may not be removed without breaking said cover.

* * * * *

UNITED STATES PATENT AND TRADEMARK OFFICE
CERTIFICATE OF CORRECTION

PATENT NO. : 5,342,584

DATED : August 30, 1994

INVENTOR(S) : Barbara L. Fritz et al.

It is certified that error appears in the above-identified patent and that said Letters Patent is hereby corrected as shown below:

On column 1, lines 5 and 6, please delete "patent application" and substitute therefore --Patent Application--

On column 1, line 6, please insert --07/703,147 filed May 17, 1991, abandoned which is a continuation-in-part of U.S. Patent Application Serial No.-- after the word "No."

On column 4, line 46, please insert --is-- after the word "which"

On column 10, line 15, please insert --138-- after the word "press"

On column 11, line 59, please delete "MAX211CPA" and substitute therefore --MAX8211CPA--

On column 13, line 38 (claim 3), please delete "35" after the word "cover"

On column 16, line 7 (claim 20), please delete "ray" and substitute therefore --tray--

On column 16, line 10 (claim 21), please delete "of polyester" after the word "of polyester"

On column 16, line 23 (claim 23), please insert --predetermined value is reached.-- after the word "said"

UNITED STATES PATENT AND TRADEMARK OFFICE
CERTIFICATE OF CORRECTION

PATENT NO. : 5,342,584
DATED : August 30, 1994
INVENTOR(S) : Barbara L. Fritz, et al It is certified that error appears in the above-indentified patent and that said Letters Patent is hereby corrected as shown below:

On column 16, line 44 (claim 26), please delete "to" and substitute therefore --top--

Signed and Sealed this

Twenty-ninth Day of November, 1994

Attest:

BRUCE LEHMAN

Attesting Officer

Commissioner of Patents and Trademarks